US012705927B2

(12) United States Patent
Suwanto et al.

(10) Patent No.: US 12,705,927 B2
(45) Date of Patent: Aug. 11, 2026

(54) METHOD FOR SELF-MEASURING FACIAL OR CORPORAL DIMENSIONS, NOTABLY FOR THE MANUFACTURING OF PERSONALIZED APPLICATORS

(71) Applicant: L'OREAL, Paris (FR)

(72) Inventors: Aldina Suwanto, Clichy (FR); Gregoire Charraud, Clichy (FR)

(73) Assignee: L'OREAL, Paris (FR)

( * ) Notice: Subject to any disclaimer, the term of this patent is extended or adjusted under 35 U.S.C. 154(b) by 960 days.

(21) Appl. No.: 17/995,285

(22) PCT Filed: Apr. 1, 2021

(86) PCT No.: PCT/EP2021/058600
§ 371 (c)(1),
(2) Date: Sep. 30, 2022

(87) PCT Pub. No.: WO2021/198412
PCT Pub. Date: Oct. 7, 2021

(65) Prior Publication Data

US 2023/0200520 A1 Jun. 29, 2023

(30) Foreign Application Priority Data

Apr. 1, 2020 (EP) .................................... 20167586

(51) Int. Cl.
*G06V 40/16* (2022.01)
*A45D 44/00* (2006.01)
(Continued)

(52) U.S. Cl.
CPC ......... *G06V 40/171* (2022.01); *A45D 44/005* (2013.01); *G06T 17/00* (2013.01);
(Continued)

(58) Field of Classification Search
None
See application file for complete search history.

(56) References Cited

U.S. PATENT DOCUMENTS 9,470,911 B2 10/2016 Fonte et al.
2012/0172685 A1 7/2012 Gilbert
(Continued)

FOREIGN PATENT DOCUMENTS

WO WO 2019/077129 A1 4/2019
WO WO 2019/077131 A1 4/2019

OTHER PUBLICATIONS

International Search Report issued Jun. 24, 2021 in PCT/EP2021/058600 filed on Apr. 1, 2021, 3 pages.

*Primary Examiner* — SJ Park
*Assistant Examiner* — Caroline E. Depalma
(74) *Attorney, Agent, or Firm* — Oblon, McClelland, Maier & Neustadt, L.L.P.

(57) ABSTRACT

Method for self-measuring dimensions of an area of keratinous materials of a user, preferably for use in the manufacturing of a personalized applicator for applying a cosmetic product, to said area of keratinous materials, the method using a mobile image capture device, and a minor, at least one characteristic dimension of said mobile image capture device being known beforehand, the method comprising: a) said mobile image capture device is placed in a predetermined position with respect to said area to be measured and in front of the minor, b) at least one image comprising said area to be measured and at least a part of said mobile image capture device is captured in the minor by said device, and c) from said at least one image, several landmark points delimiting the area to be measured are detected in order to measure at least one dimension of the
(Continued)

Figure 1:
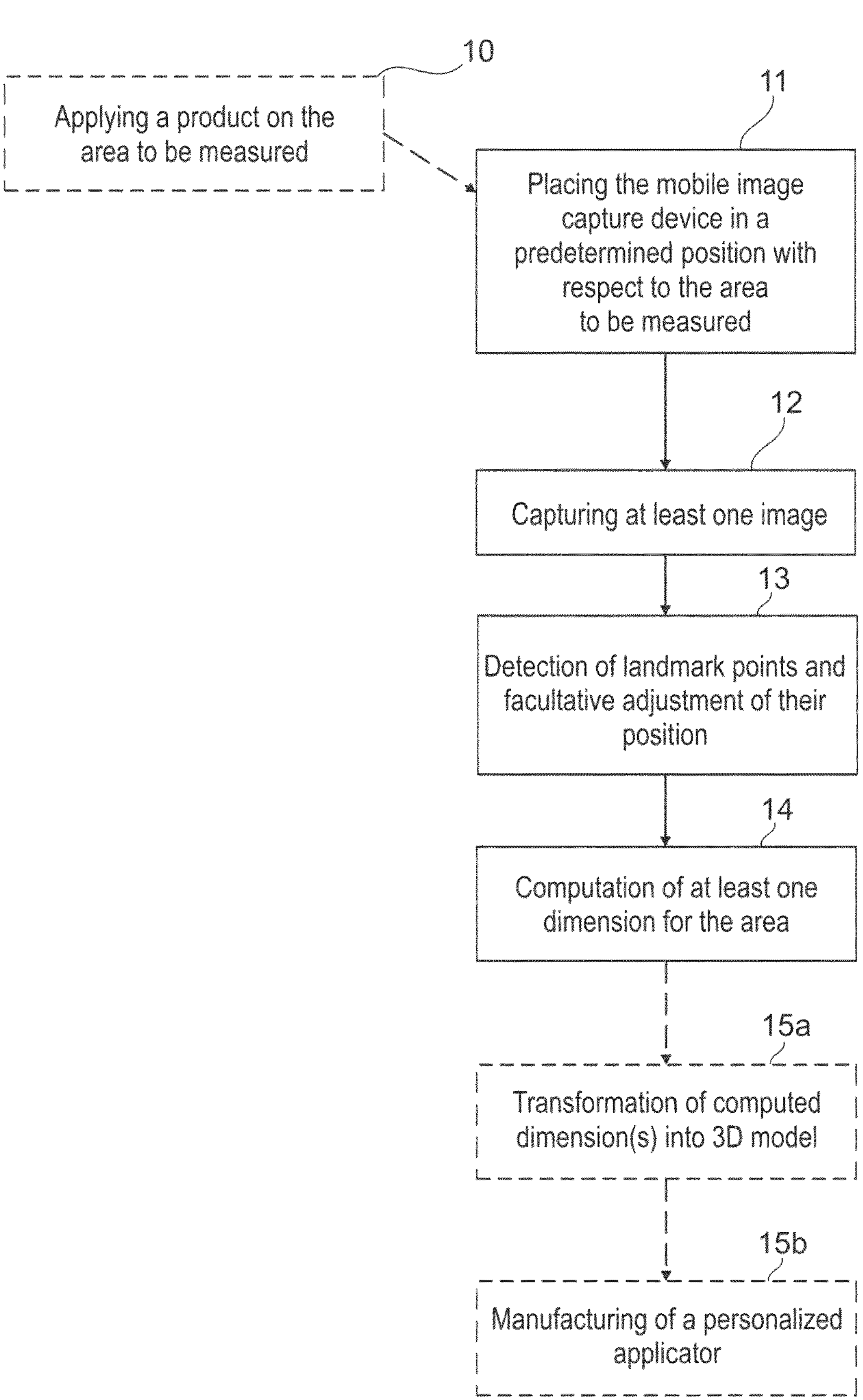

area by using at least said at least one characteristic dimension of the mobile image capture device.

18 Claims, 5 Drawing Sheets

(51) Int. Cl.

| | |
|---|---|
| ***B29C 64/393*** | (2017.01) |
| ***B33Y 50/02*** | (2015.01) |
| ***B33Y 80/00*** | (2015.01) |
| ***G06F 3/16*** | (2006.01) |
| ***G06T 17/00*** | (2006.01) |
| ***G06V 10/82*** | (2022.01) |
| ***G06V 40/60*** | (2022.01) |

(52) U.S. Cl.

CPC .............. *G06V 10/82* (2022.01); *G06V 40/67* (2022.01); *A45D 2044/007* (2013.01); *A61K 2800/80* (2013.01); *B29C 64/393* (2017.08); *B33Y 50/02* (2014.12); *B33Y 80/00* (2014.12); *G06F 3/167* (2013.01)

(56) References Cited

U.S. PATENT DOCUMENTS

| | | | | |
|---|---|---|---|---|
| 2015/0366327 | A1* | 12/2015 | Lahood, Sr. ........... | B33Y 10/00<br>264/109 |
| 2015/0382123 | A1* | 12/2015 | Jobani .................. | H04R 1/1016<br>700/98 |
| 2017/0024898 | A1* | 1/2017 | Spector ................... | G06T 7/143 |
| 2018/0117272 | A1* | 5/2018 | Fu ...................... | G06V 10/7553 |
| 2020/0260838 | A1 | 8/2020 | Samain et al. | |

* cited by examiner

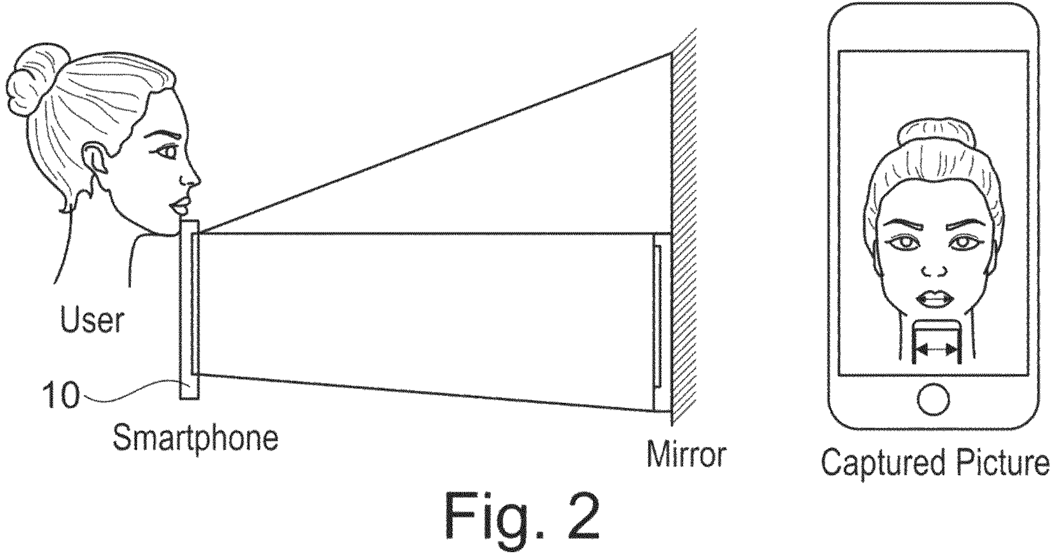
Fig. 2
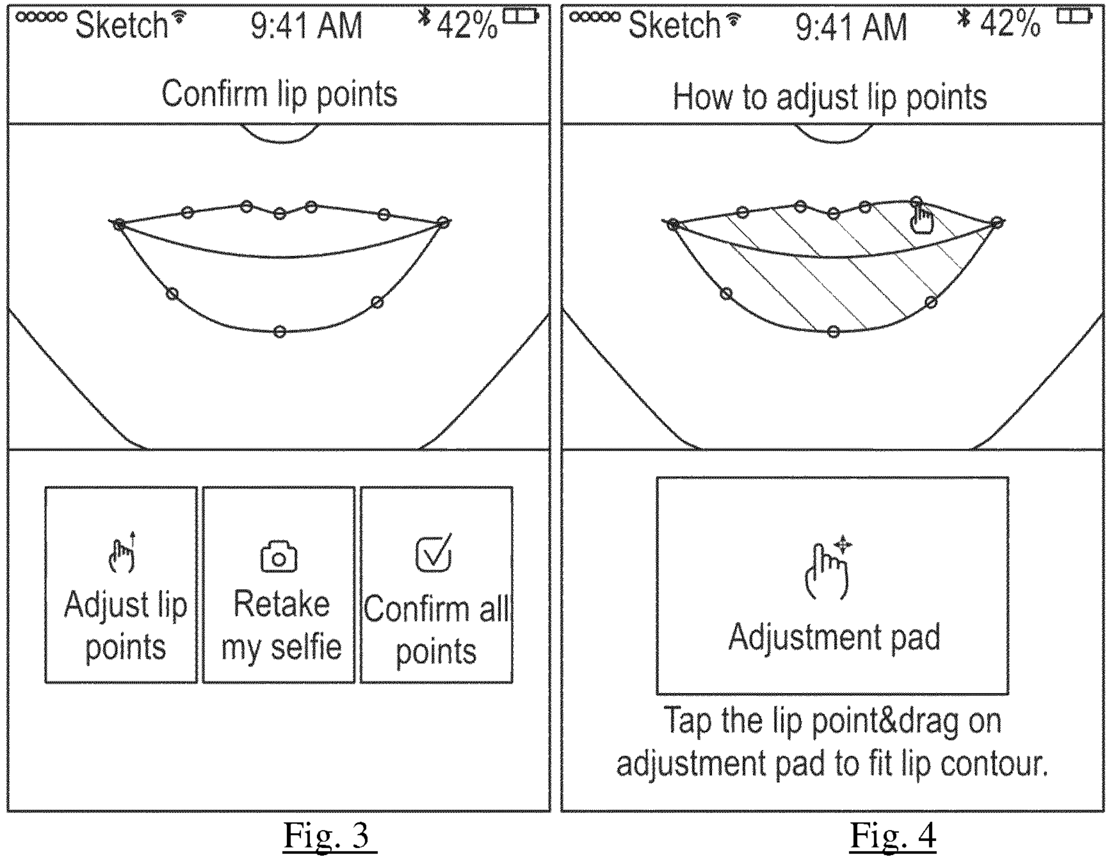
Fig. 3
Fig. 4

METHOD FOR SELF-MEASURING FACIAL OR CORPORAL DIMENSIONS, NOTABLY FOR THE MANUFACTURING OF PERSONALIZED APPLICATORS

TECHNICAL FIELD

The present invention relates to methods for self-measuring facial or corporal dimensions, notably for the manufacturing of personalized applicators for applying a cosmetic product to keratinous materials, notably the lips. The invention also relates to methods for manufacturing personalized applicators and to the cosmetic treatment methods, notably make-up, that use such applicators.

PRIOR ART

In order to apply make-up to the lips, a known method consists in applying a film of covering and/or coloring composition using an applicator such as a lip brush or a stick of lipstick, which is moved along the lips in order to cover the surface thereof. The user can see the effect obtained but may be unsatisfied with the result. In particular, if they believe that the shape of their lips does not suit them, the user remains disappointed with the result. This is what happens with users who, for example, consider their lips to be too thin, too wide, asymmetric or badly proportioned with respect to the shape of their face.

Some users consider changing the outline when applying the composition, but it is extremely difficult not to follow the natural outline of the lips. The problem is even greater with users who have difficulty with the application, for example those who have eyesight or motor skills problems. The difficulty increases further if the color of the make-up product is particularly pronounced, particularly if it is dark in color, and/or if the product is particularly hard-wearing, for example being a formulation said to be «long-lasting». In attempting to modify the outline, the chances therefore are that the results will be asymmetric or will extend beyond the natural outline to an exaggerated degree, thus rendering the result unattractive or even ridiculous.

In any case, whether the user sticks to the natural outline of the area to be treated, or whether they attempt to rectify the outline thereof, the impression of not achieving an attractive result may drive certain users to give up applying make-up. Some do not give up, but take far longer to apply their make-up, attempting to avoid the above problems. Many will need to resort to successive removals and reapplications of make-up. The procedure is therefore lengthy, irritates the mucous membranes and users are driven to applying make-up only occasionally and/or to choosing the most neutral colors possible, thus reducing the benefit of applying make-up. The same problems arise in applying make-up to the eyelids, the eyebrows or the cheekbones.

Effective methods for manufacturing personalized applicators are known from international applications WO 2019/077129 and WO 2019/077131. These methods use a 3D scan of the topography of at least part of the surface of the area to be treated, and, from at least said scan, create at least part of an applicator or a mold used for the manufacture thereof, by machining a preform or by additive manufacturing.

These solutions allow the applicators to be made available to the user quite quickly, which is important because that allows the user to be able to check the result by conducting one or more tests, particularly in the case of a desired change to the shape of their made-up lips, but also in the case of users with visual or motor-skills problems or a lack of experience. This need is also driven when the user wishes to make multiple small steps toward the solution that will best suit them. It may be advantageous to have several applicators, for example in instances in which the user has a number of different ideas about the outline and wishes to try out several results. The possibility of requesting and quickly obtaining a new personalized applicator is also attractive. Indeed, when traveling, a user will sometimes forget to bring some of their make-up, or a user may lose or damage their applicator.

Such methods for manufacturing personalized applicators need precise and complete dimensions of the concerned area, self-measured by the user with the possibility of slightly changing said dimensions, in order to then rapidly obtain a satisfactory personalized applicator.

Patent application US 2015/0382123 discloses a method for manufacturing personalized earphones based on a 3D acquisition of the area of the face that surrounds the ears of the user.

Patent application US 2012/0172685 describes methods for analyzing characteristics of the skin based on images of the user, who can take a picture of themselves, for example via their smartphone, commonly known as "selfie", and a scale guide inside the picture frame is used in order to calculate the absolute dimensions of the area of the skin to be analyzed. Such a scale guide may be a ruler or an object of known size, included in the picture frame.

U.S. Pat. No. 9,470,911 describes a method for manufacturing personalized optical glasses by using pictures of a user self-taken in front of a mirror, the size of the smartphone screen, which appears in the picture, being used to determine real anatomical dimensions from said pictures, especially by identifying the pupils, marked as landmarks. Such a method allows a precision in the range of centimeters.

More accurate dimensions are needed in the case of a personalized applicator intended to be used for applying cosmetic products in very visible areas of the face, as the lips, the cheekbones, or the areas around the eyes, as the eyebrows or eyelids.

OBJECTIVE OF THE INVENTION

There is therefore a need to easily self-measure dimensions of areas of keratinous materials of a user, that are very precise and quick to obtain, especially in order to create, in a short space of time, an applicator that is personalized to the desired shape, and yields a faithful and harmonious make-up look, notably according to the user's face.

SUMMARY OF THE INVENTION

The invention notably seeks to meet this objective and its subject, in one of its aspects, is a method for self-measuring dimensions of an area of keratinous materials of a user, preferably for use in the manufacturing of a personalized applicator for applying a cosmetic product, notably a make-up or care product, to said area of keratinous materials, the method using a mobile image capture device, notably a smartphone, and a mirror, at least one characteristic dimension of said mobile image capture device being known beforehand, the method comprising the following steps:

a) said mobile image capture device is placed in a predetermined position with respect to said area to be measured and in front of the mirror, b) at least one image comprising said area to be measured and at least a part of said mobile image capture device is captured in the mirror by said device, and c) from said at least one image, several landmark points delimiting the area to be measured are detected in order to measure at least one dimension of the area by using at least said at least one characteristic dimension of the mobile image capture device.

Thanks to the invention, users can self-measure their facial or corporal dimensions using a camera, notably a mobile phone camera, in front of a mirror, thus performing a double reflection. In particular, self-measurement of facial dimensions and acquisition of facial morphology, at home, are thus enabled with good precision for personalized make-up applicators without the need of any ruler or special property, or without the intervention of another person.

The use of a predetermined position and the knowledge of at least one characteristic dimension of said mobile image capture device bring a very high measurement accuracy, down to a few millimeters accuracy. Indeed, this offers a frame of reference for the measurements, and the same scaling factor for both the mobile device and the user's face is used, contrary to the known methods. One or several dimensions of the mobile image capture device can be easily known beforehand, notably through the model of the device.

Such facial or corporal dimensions of a user may be used to create personalized applicators perfectly fitting the user's features, especially via 3D printing, for the application of different cosmetic product, such as lipstick, eyebrow powder or ink, eyeliner, or eyelids shadows. Online purchase of such applicators from home is enabled thanks to the method of the invention, allowing easy and precise application of cosmetic products.

The method of the invention allows in particular retrieving remarkable bending points of the curvature of the lips, making it possible to perfectly define the mouth, and to color it evenly, if desired.

The invention makes it possible to achieve a professional-quality make-up look oneself, on a surface of the keratinous materials, preferably the lips, but also the eyelids or any other region of the face, for example the cheekbones, thanks to a morphological applicator tailor-made to suit the user. A make-up result with a clean outline is achieved, improving the harmony of the face. The invention also offers a way of applying make-up very quickly, in a single gesture, and anywhere, even without a mirror, for example in the car or at the office.

The invention allows make-up to be applied in bright colors and/or using a long-lasting composition without risk, even on a daily basis because personalized applicators make it possible to avoid the failures that occur when this type of product is applied using known applicators.

"An area of keratinous materials of a user" has to be understood as a region or a zone of the face or of the body of a user.

Acquisition Steps

Preferably, said mobile image capture device is placed on a same plane as the area to be measured, notably vertically and under the chin of the user for measuring an area of their face, in particular for recording dimensions of their lips.

Preferably, said mobile image capture device is placed on a plane parallel to the plane in which the mirror extends.

Information about the positioning of the mobile image capture device with respect to the area to be measured and/or the mirror may be provided during step a), notably by using a position sensor, in particular an accelerometer or a gyroscope.

One or several signals, notably voice signals, may be sent to the user to help them place the mobile image capture device in said predetermined position with respect to the area to be measured and/or with respect to the mirror. An electronic guidance for the user is thus possible.

The image is preferably automatically captured by the mobile image capture device once said predetermined position with respect to the area to be measured is reached.

Measurement and Self-Adjustment Steps

At least one dimension of said area to be measured is preferably computed based on said detected landmark points and on said at least one characteristic dimension of the mobile image capture device.

In step b), the part of said mobile image capture device comprised in the image is one part of the mobile image capture device for which said at least one characteristic dimension is known beforehand.

The outline of the area to be measured may be estimated by interpolation between said detected landmarks points.

The position of some or all of the detected landmark points may be self-adjusted by the user after step c), by using a screen of the mobile image capture device or a screen of a distant workstation connected to said mobile image capture device to which the detected landmark points have been transmitted. This allows further increasing the precision of the method according to the invention.

A mask may be applied to said area delimited by the detected landmark points, notably a mask having a color that contrasts with the color of said area, in particular a white mask. Such a color may make it easier to visualize the outline of the mask, helping the purposes of automatic outlining. The mask is preferably of a color that exhibits a pronounced contrast with the rest of the face, so that the landmark points of the area to which the mask has been applied can be detected easily.

Said mask may have an outline that changes in function of every adjusted point, while the user is self-adjusting the position of some or all of the detected landmark points. This allows the user to see in real time the result of the self-adjustment process.

The position of some or all of the detected landmark points may be automatically adjusted based on at least one option chosen by the user, as in particular the desired shape for the area to be measured, in the case of the manufacturing of a personalized applicator, notably a specific shape of Cupid's bow in the case of an application on the lips.

The invention makes it possible to redefine the outline of the concerned area, providing a remodelling effect, and can therefore be used by users whose outline has become indefinite, notably as a result of the ageing of skin, and who no longer dare to apply make-up.

Step a) may be preceded by the application of a make-up product on the area to be measured according to a predefined outline, notably a product having a color that contrasts with the color of the surroundings of said area, in particular a white product. This can help the user to choose the perfect outline for the concerned area, notably the lips. This allows a more accurate detection.

An image analysis is advantageously performed on the captured image for the detection of said landmark points, notably a contrast analysis or an object detection algorithm, in particular by using computer vision and/or facial recognition algorithms, in order to obtain the outline of said area to be measured, notably when said area is the lips.

Several images may be captured and used for a 3D reconstruction of said area.

The 3D topography of said area may be obtained based at least on the detected landmark points and/or the measured dimensions.

The detected landmark points and/or the measured dimensions are advantageously stored on the mobile image capture device and/or transmitted to a distant workstation, connected to the mobile image capture device, for the manufacturing of a personalized applicator. This allows a quick and reliable manufacturing.

The detected landmark points and/or the measured dimensions may be used by a transformation model for the generation of a 3D model to be used for the manufacturing of a personalized applicator.

A machine learning device, as in particular a classifier or a neural network, trained beforehand on several images and/or dimensions of several users, may be used by the transformation model for the generation of the 3D model. This allows obtaining a very well-fitting applicator, by inputting some relevant data into the transformation model. Such data may permit to obtain accurate dimensions for specific areas, as for example the depth of the mouth viewed from side.

The generation of the 3D model may be performed remotely using software from a distant workstation to which the detected landmark points and/or the measured dimensions have been transmitted over a telecommunications network, notably over the Internet or by GSM/GPRS.

A specific pattern may be displayed on the screen of the mobile image capture device, as specific shapes or QR codes-like displays, during the image acquisition to increase robustness of screen detection. Said specific pattern needing to be fully detected, an error message may appear to tell the user to redo the acquisition under better condition, notably in case there is any light reflection on the screen of said mobile image capture, notably hiding partially the specific pattern.

In the case of the lips, the possible measured dimensions may be their length between the two extreme points, the upper lip height at different points along the lips, the height of the cupid's bow, the distance of philtrum ridge from lip midline, the lower lip height at different points along the lips, the distance from the lip corner at different points along the lips, and/or the height of the commissure from the highest lip point.

An automatic selection process for the applicator may be implemented, comprising choosing the closest neighbour from a group of predefined applicators, based on several computed dimensions. Indeed, for example for a granularity equal to 1 mm, there are hundreds of millions of models to be selected.

In a variant, some dimension may be linked to another dimension by ratio based on a correlation analysis or the use of machine learning. The number of models from which the applicator will be selected may thus be reduced. This approach is more scalable and efficient, as it avoids, in particular, the need to create a 3D model each time and the need of 3D-modelling software license at the manufacturing station.

Self-Measurement System

According to another of its aspects, a subject of the invention is a system for self-measuring dimensions of an area of keratinous materials of a user, preferably for use in the manufacturing of a personalized applicator for applying a cosmetic product, notably a make-up or care product, to said area of keratinous materials, the system comprising a mobile image capture device, notably a smartphone, and using a mirror, at least one characteristic dimension of said mobile image capture device being known beforehand, system characterized in that, once said mobile image capture device is placed in a predetermined position with respect to said area to be measured and in front of the mirror, said mobile image capture device is able to capture in the mirror at least one image comprising said area to be measured and at least a part of said mobile image capture device, and the system being able to detect, from said at least one image, several landmark points delimiting the area to be measured, in order to measure at least one dimension of the area by using at least said at least one characteristic dimension of the mobile image capture device.

The mobile image capture device may be a smartphone camera, a camera or a surface pad. However, the invention is not limited to a specific kind of mobile image capture device.

The mobile image capture device, especially in the case of a smartphone, may include one or more microprocessors or microcontrollers and additional circuits, arranged to execute an application aimed at performing the steps of the method according to the invention.

The features described above in relation with the method for self-measuring dimensions apply to the system and vice versa Computer Program Product According to yet another of its aspects, a subject of the invention is a computer program product for self-measuring dimensions of an area of keratinous materials of a user, preferably for use in the manufacturing of a personalized applicator for applying a cosmetic product, notably a make-up or care product, to said area of keratinous materials, by using a mobile image capture device, notably a smartphone, and a mirror, at least one characteristic dimension of said mobile image capture device being known beforehand, the computer program product comprising a support and stored on this support instructions that can be read by a processor, these instructions being configured for:

a) placing said mobile image capture device in a predetermined position with respect to said area to be measured and in front of the mirror,
b) having at least one image comprising said area to be measured and at least a part of said mobile image capture device being captured in the mirror by said device, and
c) detecting, from said at least one image, several landmark points delimiting the area to be measured, in order to measure at least one dimension of the area by using at least said at least one characteristic dimension of the mobile image capture device.

The features described above in relation with the method for self-measuring dimensions apply to the computer program product and vice versa.

Method for Manufacturing Applicators

Another subject of the invention is a method for manufacturing a personalized applicator for applying a product, notably a make-up or care product, to an area of keratinous materials of a user, the method comprising a step of creating the applicator or a mold intended for the manufacture thereof, by machining a preform or by additive manufacturing, by using the detected landmark points and/or the dimensions of said area obtained according to the method for self-measuring dimension as described above.

The applicator may be produced by machining, preferably by micro-machining. A preform chosen, notably automatically, from among several preforms according to the shape that is to be obtained after machining, may be machined. This makes it possible to shorten the manufacturing time.

In a variant, the applicator or the mold intended for its manufacture is produced by 3D printing.

A file that can be read by a CNC machine (Computer Numerical Control machine) or a 3D printer is advantageously generated and can be stored, notably automatically, for example in the cloud or on a central server, and sent to all user access points, for example sales outlets or institutes. The file may be sent to the user. It is also possible to keep files not adopted, in order to avoid redundant testing.

The applicator may be produced with a handle on the back. Said handle may be removable or may attach with a clip.

One or more distinctive signs, such as a maker and/or a forename, may be inscribed on the applicator, for example so as to be able to recognise the maker and/or the owner.

The features described above in relation with the method and system for self-measuring dimensions apply to the manufacturing method and vice versa.

Method for Applying a Product

A further subject of the invention is a method of applying a make-up or care product using an applicator obtained by implementing the manufacturing method as defined above, involving bringing the applicator into contact with said area of keratinous materials of the user and transferring the product onto said area.

The applicator preferably becomes laden with product by being brought into contact with a pad soaked in product.

The make-up applying method can be implemented for applying make-up to the lips, said keratinous materials comprising at least part of the lips and, better, of an adjacent area of skin.

Yet another subject of the invention is a method for applying a make-up product to the lips, in which method the outline of the lips is defined using an applicator, manufactured as defined hereinabove, comprising an application surface to be pressed against the lips, configured to apply the product only at their periphery so as to apply make-up to their outline only, by loading the application surface with product and pressing it against the lips.

Such an applicator allows the lips to be outlined with make-up quickly and accurately in a single gesture by pressing the applicator against the lips.

DETAILED DESCRIPTION

Figure 8:
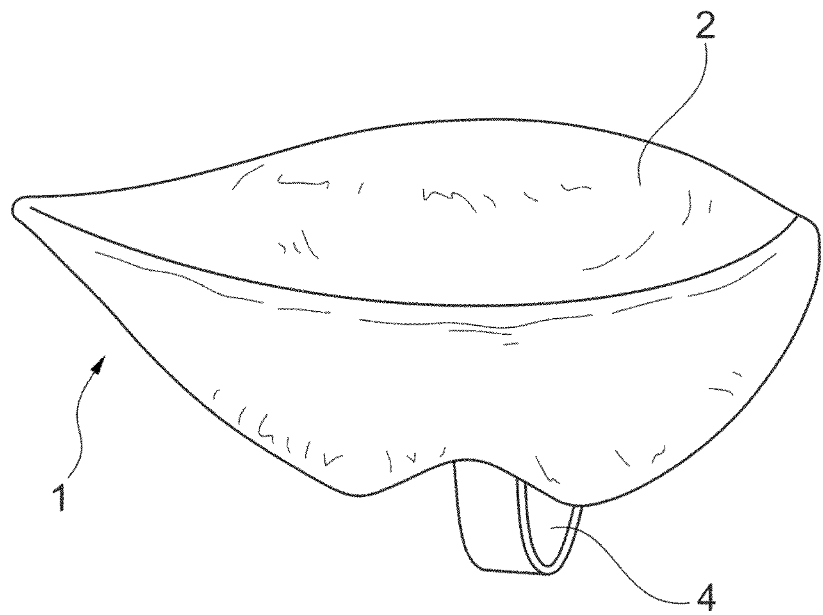

The invention will be better understood from reading the following detailed description of nonlimiting embodiments thereof and from studying the attached drawing, in which:

FIG. 1 is an illustration of various steps of an example of a method for self-measuring dimensions according to the invention, FIG. 2 shows an implementation of the method for self-measuring dimensions according to the invention, FIGS. 3 to 7 illustrate screens of a mobile application aimed at performing the steps of the method according to the invention, and FIG. 8 illustrates an applicator manufactured by 3D printing and by using dimensions self-measured according to the invention.

Various steps in an example of a method, according to the invention, for self-measuring dimensions are depicted in FIG. 1 and will be described in detail in what follows. The method uses a mobile image capture device, notably a smartphone, and a mirror, at least one characteristic dimension of said mobile image capture device being known beforehand.

During a step 11, said mobile image capture device is placed in a predetermined position with respect to said area to be measured and in front of the mirror. The predetermined position preferably corresponds to a same plane as the area to be measured, for example vertically and under the chin of the user for measuring an area of their face. Said mobile image capture device is also placed on a plane parallel to the plane in which the mirror extends, as can be seen in FIG. 2.

In this example and as previously described, information about the positioning of the mobile image capture device with respect to the area to be measured and/or the mirror is provided during step 11, by using a position sensor, as an accelerometer or a gyroscope. One or several voice signals are consequently sent to the user to help them place the mobile image capture device in said predetermined position with respect to the area to be measured and/or with respect to the mirror.

During a step 12, at least one image comprising the area to be measured and at least a part of said mobile image capture device is captured in the mirror by the mobile image capture device, as can be seen in FIG. 2. Preferably, the image is automatically captured by the mobile image capture device once said predetermined position with respect to the area to be measured is reached.

In a step 13, from said at least one image, several landmark points delimiting the area to be measured are detected. To this end, an image analysis is advantageously performed on the captured image, notably a contrast analysis or an object detection algorithm, in particular by using computer vision and/or facial recognition algorithms.

The position of some or all of the detected landmark points may be self-adjusted by the user, by using a screen of the mobile image capture device or a screen of a distant workstation connected to said mobile image capture device to which the detected landmark points have been transmitted. To assist the user during this step, a mask may be applied to said area delimited by the detected landmark points, notably a mask having a color that contrasts with the color of said area, in particular a white mask. The outline of the mask advantageously changes in function of every adjusted point, while the user is self-adjusting the position of some or all of the detected landmark points.

In a variant or in combination, the position of some or all of the detected landmark points may automatically be adjusted based on at least one option chosen by the user, as in particular the desired shape for the area to be measured, in the case of the manufacturing of a personalized applicator, notably a specific shape of Cupid's bow in the case of an application on the lips.

At least one dimension of said area to be measured is then computed, during a step 14, based on said detected landmark points and on said at least one characteristic dimension of the mobile image capture device.

Step 11 may be preceded by a step 10 of application of a make-up product on the area to be measured according to a predefined outline, notably a product having a color that contrasts with the color of the surroundings of said area, in particular a white product. This allows a more accurate acquisition.

In this example, during a step 15*b*, the detected landmark points and/or the measured dimensions are used for the manufacturing of a personalized applicator. They may be stored on the mobile image capture device and/or transmitted to a distant workstation, connected to the mobile image capture device.

The detected landmark points and/or the measured dimensions may be used by a transformation model for the generation of a 3D model to be used for the manufacturing of a personalized applicator, as illustrated by the step 15*a* of FIG. 1. The generation of the 3D model may be performed remotely using software from a distant workstation to which the detected landmark points and/or the measured dimensions have been transmitted over a telecommunications network, notably over the Internet or by GSM/GPRS.

The manufacturing of a personalized applicator may comprise the creation of the applicator or of a mold intended for the manufacture thereof, by machining a preform or by additive manufacturing, for example by 3D printing, by using the detected landmark points and/or the dimensions of said area hence obtained.

FIG. 2 shows a mobile image capture device 10, namely a smartphone, placed under the chin of a user and in front of a mirror, in order to capture, in said mirror, an image comprising an area to be measured and at least a part of said mobile image capture device 10. In this example, the area is the lips and the captured image, as shown, will help computing at least one dimension of the lips, their length between the two extreme points, based on the knowledge of one characteristic dimension of said mobile image capture device 10, its transverse dimension.

Example

In an example illustrated by FIGS. 3 to 7, a user who wants to buy a personalized applicator for applying a make-up product to their lips follows the screens of a mobile application aimed at performing the steps of the method according to the invention and executed on their smartphone comprising an image capture device.

On the home screen of the mobile application, the user enters his name, which is recorded to be associated with the detected landmark points and/or the measured dimensions. Following the home screen, an instruction screen appears, explaining how to take the image, called "selfie", with in particular three rules to follow: closed mouth, no smiling, phone on chin, corresponding to the preferred predetermined position for measuring the lips. Then appears a splash screen indicating to the user that, whenever ready, they can turn the phone so that its back faces the mirror. The splash screen changes after 3 seconds to a selfie screen, or the user can tap the screen to skip to the next one.

The smartphone is then set on a selfie screen, not visible to the user, which comprises a positioning mask to indicate the predetermined position with respect to the area to be measured. The image is automatically captured, after a countdown. A processing screen appears next while the landmark points are detected, which lasts about 3 seconds. The next screen shows the detected landmark points, for example in white bullets, as can be seen in FIG. 3. The user, via three option buttons, can either choose to retake the selfie, confirm all the points or adjust some or all of them.

Figure 5:
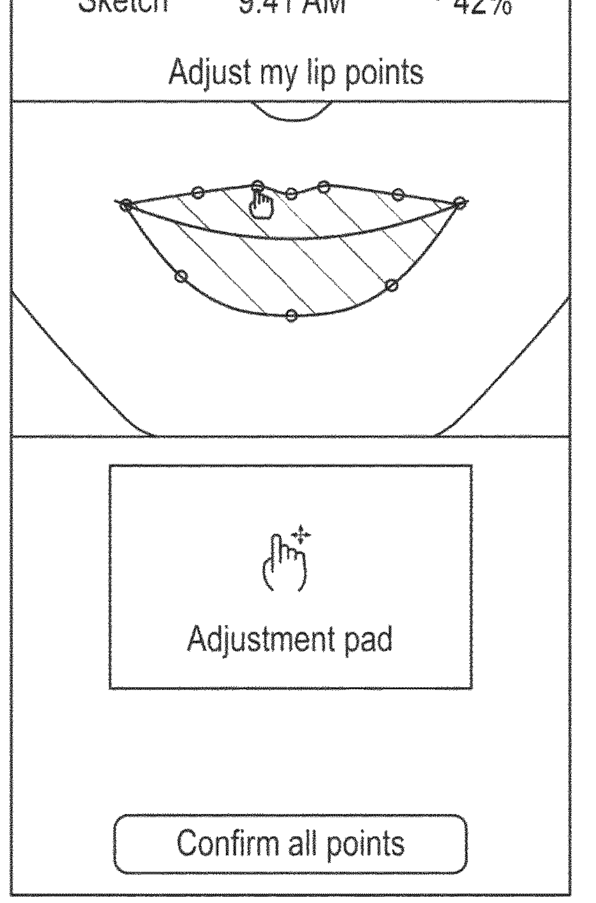

In the last case, as can be seen in FIG. 4, a new screen appears which presents an adjustment pad allowing the user to move some or all of the points. A white transparent mask is formed to highlight the outline of the area thanks to the detected landmark points. The user can then move the desired points, as shown in FIG. 5, the mask changing for every adjusted point, while the user is self-adjusting the position of some or all of the detected landmark points.

Figure 6:
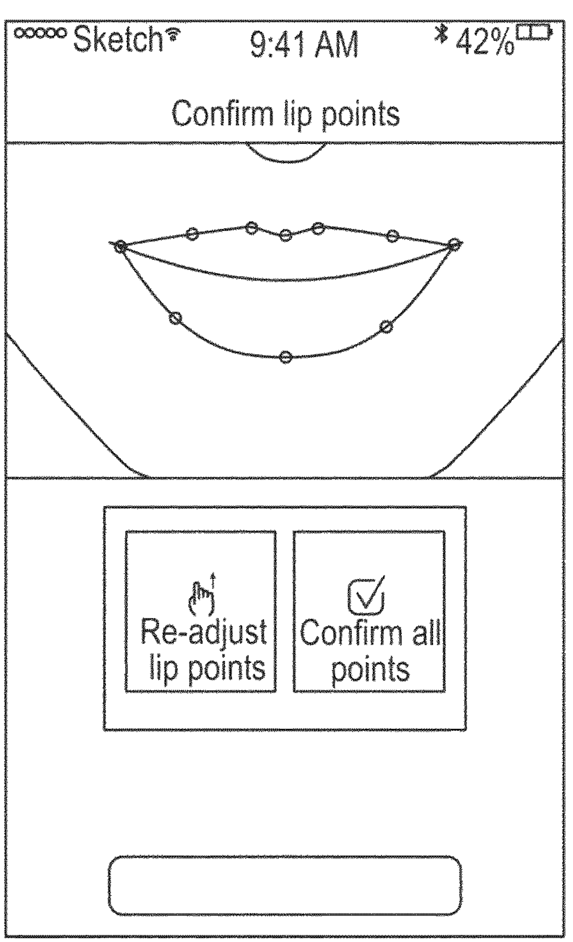
Figure 7:
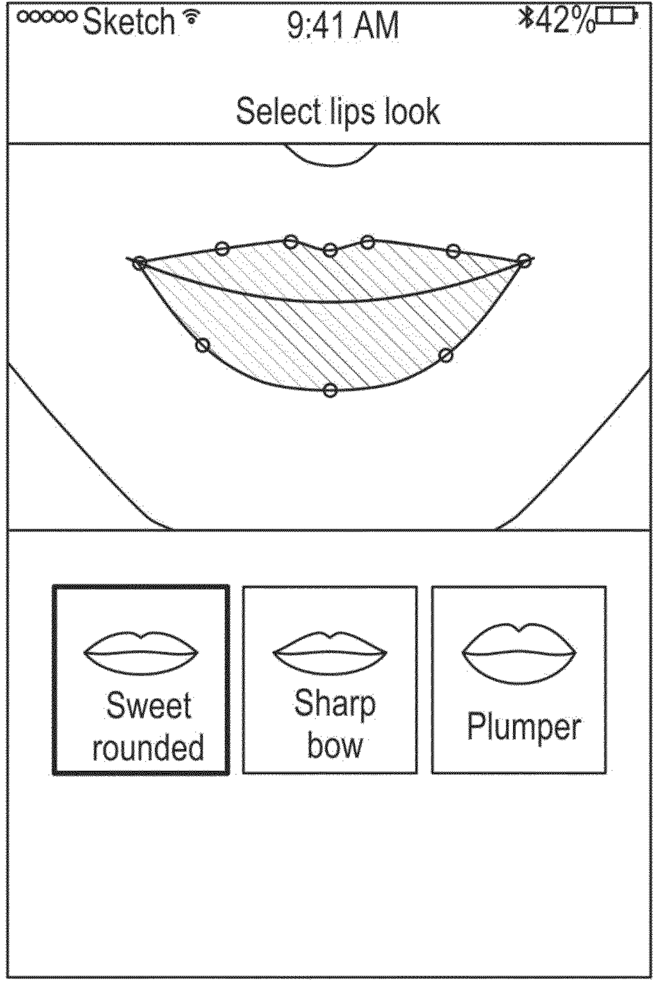

When the result is satisfactory, the user taps a button "confirm all the points" and a new screen showing the area outlined by the landmark points appears, as well as two option buttons for either re-adjusting the points or confirm all the points, as visible in FIG. 6. Once confirmed, the screen of FIG. 7 appears, with a red mask with transparency highlighting the lips, and three look options for the user: sweet rounded, sharp bow, plumper, which can lead to an automatic adjusting of the registered landmark points. The final data are then registered, and the user can go back to the home screen.

An example of an applicator 1 manufactured by using dimensions self-measured according to the invention is shown in FIG. 8.

The applicator 1, intended to be used for applying a lipstick on the lips, comprises an application surface 2 and a handle 4. In this example, the manufacturing was performed by 3D printing.

When the user wants to apply lipstick, they can load the applicator with product, preferably by bringing it into contact with a pad soaked in product, and then bring the applicator into contact with their lips for transferring the product thereof.

Of course, the invention is not limited to the exemplary embodiments that have just been described.

The invention may be used to manufacture different kinds of applicators, intended to be used for applying specific products on specific areas of the keratinous materials.

The self-measuring method according to the invention may also be used to get absolute measurements of wrinkles length, spots, or acne lesions, for skin diagnostic purposes.

The invention claimed is:

1. A method for self-measuring dimensions of an area of keratinous materials of a user, the method using a mobile image capture device and a mirror, at least one characteristic dimension of said mobile image capture device being known beforehand through the model of the device, the method comprising the following steps:

a) said mobile image capture device is placed in a predetermined position with respect to said area to be measured and in front of the mirror, b) at least one image comprising said area to be measured and at least a part of said mobile image capture device is captured in the mirror by said device, and c) from said at least one image, several landmark points delimiting the area to be measured are detected in order to measure at least one dimension of the area by using at least said at least one characteristic dimension of the mobile image capture device, wherein the position of some or all of the detected landmark points is self-adjusted by the user after step c), by using a screen of the mobile image capture device or a screen of a distant workstation connected to said mobile image capture device to which the detected landmark points have been transmitted.

2. The method as claimed in claim 1, wherein said mobile image capture device is placed on a same plane as the area to be measured.

3. The method as claimed in claim 2, wherein said mobile image capture device is placed vertically and under the chin of the user for measuring an area of their face.

4. The method as claimed in claim 1, wherein said mobile image capture device is placed on a plane parallel to the plane in which the mirror extends.

5. The method as claimed in claim 1, wherein information about the positioning of the mobile image capture device with respect to the area to be measured and/or the mirror is provided during step a).

6. The method as claimed in claim 5, wherein said information is provided by using a position sensor.

7. The method as claimed in claim 1, wherein one or several signals are sent to the user to help them place the mobile image capture device in said predetermined position with respect to the area to be measured and/or with respect to the mirror.

8. The method as claimed in claim 1, wherein the image is automatically captured by the mobile image capture device once said predetermined position with respect to the area to be measured is reached.

9. The method as claimed in claim 1, wherein at least one dimension of said area to be measured is computed based on said detected landmark points and on said at least one characteristic dimension of the mobile image capture device.

10. The method as claimed in claim 1, wherein a mask is applied to said area delimited by the detected landmark points.

11. A method for manufacturing a personalized applicator for applying a product to an area of keratinous materials of a user, the method comprising a step of creating the applicator or a mold intended for the manufacture thereof, by machining a preform or by additive manufacturing, by using the detected landmark points and/or the dimensions of said area obtained according to the method of claim 1.

12. The method as claimed in claim 1, being for use in the manufacturing of a personalized applicator for applying a cosmetic product to said area of keratinous materials.

13. The method as claimed in claim 12, wherein said cosmetic product is a make-up or care product.

14. The method as claimed in claim 1, wherein said mobile image capture device is a smartphone.

15. A system for self-measuring dimensions of an area of keratinous materials of a user, the system comprising a mobile image capture device, and using a mirror, at least one characteristic dimension of said mobile image capture device being known beforehand through the model of the device, system characterized in that, once said mobile image capture device is placed in a predetermined position with respect to said area to be measured and in front of the mirror, said mobile image capture device is able to capture in the mirror at least one image comprising said area to be measured and at least a part of said mobile image capture device, and the system being able to detect, from said at least one image, several landmark points delimiting the area to be measured, in order to measure at least one dimension of the area by using at least said at least one characteristic dimension of the mobile image capture device, wherein the position of some or all of the detected landmark points is self-adjusted by the user after detecting the several landmark points, by using a screen of the mobile image capture device or a screen of a distant workstation connected to said mobile image capture device to which the detected landmark points have been transmitted.

16. A non-transitory computer-readable medium for self-measuring dimensions of an area of keratinous materials of a user, by using a mobile image capture device and a mirror, at least one characteristic dimension of said mobile image capture device being known beforehand through the model of the device, the computer-readable medium comprising a support and stored on this support instructions that can be read by a processor, these instructions being configured for:

a) placing said mobile image capture device in a predetermined position with respect to said area to be measured and in front of the mirror, b) having at least one image comprising said area to be measured and at least a part of said mobile image capture device being captured in the mirror by said device, and c) detecting, from said at least one image, several landmark points delimiting the area to be measured, in order to measure at least one dimension of the area by using at least said at least one characteristic dimension of the mobile image capture device, wherein the position of some or all of the detected landmark points is self-adjusted by the user after step c), by using a screen of the mobile image capture device or a screen of a distant workstation connected to said mobile image capture device to which the detected landmark points have been transmitted.

17. A method for self-measuring dimensions of an area of keratinous materials of a user, the method using a mobile image capture device and a mirror, at least one characteristic dimension of said mobile image capture device being known beforehand through the model of the device, the method comprising the following steps:

a) said mobile image capture device is placed in a predetermined position with respect to said area to be measured and in front of the mirror, b) at least one image comprising said area to be measured and at least a part of said mobile image capture device is captured in the mirror by said device, and c) from said at least one image, several landmark points delimiting the area to be measured are detected in order to measure at least one dimension of the area by using at least said at least one characteristic dimension of the mobile image capture device, wherein step a) is preceded by the application of a make-up product on the area to be measured according to a predefined outline.

18. A method for self-measuring dimensions of an area of keratinous materials of a user, the method using a mobile image capture device and a mirror, at least one characteristic dimension of said mobile image capture device being known beforehand through the model of the device, the method comprising the following steps:

a) said mobile image capture device is placed in a predetermined position with respect to said area to be measured and in front of the mirror, b) at least one image comprising said area to be measured and at least a part of said mobile image capture device is captured in the mirror by said device, and c) from said at least one image, several landmark points delimiting the area to be measured are detected in order to measure at least one dimension of the area by using at least said at least one characteristic dimension of the mobile image capture device, wherein the detected landmark points and/or the measured dimensions are used by a transformation model for the generation of a 3D model to be used for the manufacturing of a personalized applicator, and a machine learning device, trained beforehand on several images and/or dimensions of several users, being used by the transformation model for the generation of the 3D model.

* * * * *